US009566421B2

(12) United States Patent
Casey et al.

(10) Patent No.: US 9,566,421 B2
(45) Date of Patent: Feb. 14, 2017

(54) FLUID APPLICATION DEVICE AND METHOD

(71) Applicant: Otsuka America Pharmaceutical, Inc., Rockville, MD (US)

(72) Inventors: Ronald J. Casey, Silver Spring, MD (US); Patrick P. Vanek, Frederick, MD (US); Royal D. Hathaway, Montgomery Village, MD (US); David L. Foshee, Apex, NC (US); Theodore J. Mosler, Raleigh, NC (US); Nicholas J. Jardine, Cary, NC (US); Kristin L. Benokraitis, Durham, NC (US)

(73) Assignee: Otsuka America Pharmaceutical, Inc., Rockville, MD (US)

(*) Notice: Subject to any disclaimer, the term of this patent is extended or adjusted under 35 U.S.C. 154(b) by 434 days.

(21) Appl. No.: 13/965,821

(22) Filed: Aug. 13, 2013

(65) Prior Publication Data

US 2013/0330114 A1 Dec. 12, 2013

Related U.S. Application Data

(62) Division of application No. 12/654,660, filed on Dec. 29, 2009, now Pat. No. 8,858,484.

(60) Provisional application No. 61/141,540, filed on Dec. 30, 2008.

(51) Int. Cl.
| | | |
|---|---|---|
| *A61M 35/00* | (2006.01) | |
| *A61M 5/178* | (2006.01) | |
| *B67B 7/00* | (2006.01) | |
| *B65D 35/54* | (2006.01) | |
| *A61F 13/40* | (2006.01) | |
| *A45D 34/00* | (2006.01) | |
| *B65D 47/42* | (2006.01) | |
| *B65D 83/00* | (2006.01) | |

(52) U.S. Cl.
CPC ............ *A61M 35/006* (2013.01); *A45D 34/00* (2013.01); *A61M 35/003* (2013.01); *B65D 47/42* (2013.01); *B65D 83/0055* (2013.01); *A45D 2200/1009* (2013.01); *A45D 2200/1018* (2013.01); *A61M 35/00* (2013.01)

(58) Field of Classification Search
CPC ...... A61F 13/40; A61M 35/00; A61M 35/006; A61M 35/003; A45D 2200/1009; A45D 2200/1018; B65D 47/42
USPC ............................... 604/1–3, 185; 222/1, 96
See application file for complete search history.

(56) References Cited

U.S. PATENT DOCUMENTS

| | | |
|---|---|---|
| 359,527 A | 3/1887 | Wirz |
| 1,715,914 A | 6/1929 | Halk |
| 2,180,248 A | 11/1939 | Layne |
| 2,218,362 A | 10/1940 | Vredenburgh |

(Continued)

FOREIGN PATENT DOCUMENTS

| | | |
|---|---|---|
| CA | 1 202 275 A | 3/1986 |
| CA | 1284784 | 6/1991 |

(Continued)

OTHER PUBLICATIONS

European Search Report for European Application No. 13176081.1 dated Nov. 7, 2013.

(Continued)

*Primary Examiner* — Jacqueline Stephens

(57) ABSTRACT

The present invention provides a device, a system, and a method for application of fluids.

24 Claims, 13 Drawing Sheets

(56) References Cited

U.S. PATENT DOCUMENTS

| | | |
|---|---|---|
| 2,568,328 A | 9/1951 | Elby |
| 2,783,489 A | 3/1957 | Bogoslowsky |
| 3,080,179 A | 3/1963 | Deutsch |
| 3,152,352 A | 10/1964 | Kosik, Jr. |
| 3,325,031 A | 6/1967 | Singier |
| 3,386,793 A | 6/1968 | Stanton |
| 3,466,131 A | 9/1969 | Arcudi |
| 3,481,876 A | 12/1969 | Schwartzman |
| 3,613,685 A | 10/1971 | Reynolds |
| 3,647,305 A | 3/1972 | Baker et al. |
| 3,647,605 A | 3/1972 | Spiegel |
| 3,687,140 A | 8/1972 | Reynolds |
| 3,757,782 A | 9/1973 | Aiken |
| 3,774,609 A | 11/1973 | Schwartzman |
| 3,826,259 A | 7/1974 | Bailey |
| 3,891,331 A | 6/1975 | Avery |
| 3,901,233 A | 8/1975 | Grossan |
| 3,929,135 A | 12/1975 | Thompson |
| D245,221 S | 8/1977 | Hoyt |
| 4,127,339 A | 11/1978 | Malacheski et al. |
| 4,148,318 A | 4/1979 | Meyer |
| 4,183,684 A | 1/1980 | Avery, Jr. |
| 4,219,283 A | 8/1980 | Buckley et al. |
| 4,291,697 A | 9/1981 | Georgevich |
| 4,304,869 A | 12/1981 | Dyke |
| 4,427,115 A | 1/1984 | Laipply |
| 4,430,013 A | 2/1984 | Kaufman |
| 4,519,795 A | 5/1985 | Hitchcock, Jr. et al. |
| 4,594,835 A | 6/1986 | Gray |
| 4,643,725 A | 2/1987 | Schlesser et al. |
| D288,780 S | 3/1987 | Miller |
| 4,648,506 A | 3/1987 | Campbell |
| 4,696,393 A | 9/1987 | Laipply |
| 4,701,168 A | 10/1987 | Gammons |
| D292,672 S | 11/1987 | Duell |
| 4,787,536 A | 11/1988 | Widerstrom |
| 4,812,067 A | 3/1989 | Brown et al. |
| 4,869,612 A | 9/1989 | Mooney et al. |
| 4,875,602 A | 10/1989 | Chickering et al. |
| 4,896,768 A | 1/1990 | Anderson |
| 4,921,137 A | 5/1990 | Heijenga |
| 4,925,327 A | 5/1990 | Wirt |
| 4,927,283 A | 5/1990 | Fitjer |
| 4,957,385 A | 9/1990 | Weinstein |
| 4,963,045 A | 10/1990 | Willcox |
| 5,087,138 A | 2/1992 | Terbrusch et al. |
| 5,098,297 A | 3/1992 | Chari et al. |
| 5,135,112 A | 8/1992 | Kamen et al. |
| 5,135,472 A | 8/1992 | Hermann et al. |
| 5,181,621 A | 1/1993 | Plaehn |
| 5,215,221 A | 6/1993 | Dirksing |
| 5,288,159 A | 2/1994 | Wirt |
| 5,308,611 A | 5/1994 | Thompson |
| D351,338 S | 10/1994 | Koptis |
| 5,376,686 A | 12/1994 | Ishikawa et al. |
| 5,435,660 A | 7/1995 | Wirt |
| 5,489,280 A | 2/1996 | Russell |
| 5,509,744 A | 4/1996 | Frazier |
| 5,577,851 A | 11/1996 | Koptis |
| 5,597,255 A | 1/1997 | Yager et al. |
| 5,616,348 A | 4/1997 | Winicov |
| 5,658,084 A | 8/1997 | Wirt |
| D386,849 S | 11/1997 | Dehavilland |
| 5,702,404 A | 12/1997 | Willingham |
| 5,713,843 A | 2/1998 | Vangsness |
| D396,126 S | 7/1998 | Ohmart |
| 5,775,826 A | 7/1998 | Miller |
| D396,911 S | 8/1998 | DeHavilland |
| 5,791,801 A | 8/1998 | Miller |
| 5,800,825 A | 9/1998 | McMullen |
| 5,829,902 A | 11/1998 | Fomby |
| 5,908,256 A | 6/1999 | Bernstein |
| 5,916,882 A | 6/1999 | Jeng |
| 5,961,235 A | 10/1999 | Kennedy |
| D416,389 S | 11/1999 | Frazier |
| 6,019,765 A | 2/2000 | Thornhill et al. |
| 6,039,488 A | 3/2000 | Krawczyk et al. |
| 6,126,633 A | 10/2000 | Kaji et al. |
| D434,525 S | 11/2000 | Angeletta |
| 6,155,990 A | 12/2000 | Fournier |
| 6,248,085 B1 | 6/2001 | Scholz et al. |
| D448,521 S | 9/2001 | Angeletta |
| 6,315,480 B1 | 11/2001 | Martel et al. |
| 6,371,675 B1 | 4/2002 | Hoang et al. |
| 6,415,470 B1 | 7/2002 | Ramrattan |
| 6,419,642 B1 | 7/2002 | Marchitto et al. |
| 6,422,778 B2 | 7/2002 | Baumann et al. |
| D461,596 S | 8/2002 | Angeletta |
| D467,613 S | 12/2002 | Indegno et al. |
| 6,488,665 B1 | 12/2002 | Severin et al. |
| 6,503,013 B2 | 1/2003 | Strauss |
| 6,505,985 B1 | 1/2003 | Hidle et al. |
| 6,523,550 B2 | 2/2003 | McCormick |
| 6,533,484 B1 | 3/2003 | Osei et al. |
| 6,536,975 B1 | 3/2003 | Tufts |
| 6,546,588 B1 | 4/2003 | Black |
| 6,547,468 B2 | 4/2003 | Gruenbacher et al. |
| 6,595,940 B1 | 7/2003 | D'Alessio et al. |
| D481,165 S | 10/2003 | Angeletta |
| D481,166 S | 10/2003 | Angeletta |
| 6,672,784 B2 | 1/2004 | Baumann et al. |
| 6,682,695 B2 | 1/2004 | MacPhee et al. |
| 6,708,822 B1 | 3/2004 | Muni |
| D490,561 S | 5/2004 | Angeletta |
| D490,562 S | 5/2004 | Angeletta |
| 6,729,786 B1 | 5/2004 | Tufts et al. |
| 6,755,586 B1 | 6/2004 | Frazier |
| 6,773,189 B1 | 8/2004 | Tsaur |
| D498,021 S | 11/2004 | Angeletta |
| 6,902,335 B2 | 6/2005 | Bergey et al. |
| 6,910,822 B2 | 6/2005 | Hidle et al. |
| 6,916,133 B2 | 7/2005 | Hoang et al. |
| 6,929,475 B1 | 8/2005 | Dragan |
| 6,960,041 B2 | 11/2005 | Tsaur |
| D512,794 S | 12/2005 | Angeletta |
| 6,991,393 B2 | 1/2006 | Tufts et al. |
| 6,991,394 B2 | 1/2006 | Tufts et al. |
| 6,992,233 B2 | 1/2006 | Drake et al. |
| D519,283 S | 4/2006 | Watson |
| 7,040,827 B2 | 5/2006 | Gueret |
| D527,489 S | 8/2006 | Angeletta |
| 7,090,422 B2 | 8/2006 | Baumann et al. |
| D527,842 S | 9/2006 | Angeletta |
| 7,108,440 B1 | 9/2006 | Gruenbacher et al. |
| D536,481 S | 2/2007 | Angeletta |
| 7,182,536 B2 | 2/2007 | Tufts et al. |
| 7,201,525 B2 | 4/2007 | Mohiuddin |
| D543,658 S | 5/2007 | Angeletta |
| D547,003 S | 7/2007 | Angeletta |
| 7,261,701 B2 | 8/2007 | Davis et al. |
| D558,393 S | 12/2007 | Angeletta |
| D566,330 S | 4/2008 | Angeletta |
| 7,377,710 B2 | 5/2008 | Baumann et al. |
| 2001/0012851 A1 | 8/2001 | Lundy et al. |
| 2001/0050083 A1 | 12/2001 | Marchitto et al. |
| 2001/0055511 A1 | 12/2001 | Baumann et al. |
| 2002/0044816 A1 | 4/2002 | Strauss |
| 2002/0114657 A1 | 8/2002 | Gueret |
| 2003/0015605 A1 | 1/2003 | Garcia et al. |
| 2003/0086747 A1 | 5/2003 | Baumann et al. |
| 2003/0095826 A1 | 5/2003 | Policicchio et al. |
| 2003/0123919 A1 | 7/2003 | Gueret |
| 2004/0068218 A1 | 4/2004 | Davis et al. |
| 2004/0071494 A1 | 4/2004 | Staniforth et al. |
| 2004/0074033 A1 | 4/2004 | Steinberg |
| 2004/0086321 A1 | 5/2004 | Burkholz et al. |
| 2004/0114988 A1 | 6/2004 | Baumann et al. |
| 2004/0162533 A1 | 8/2004 | Alley |
| 2004/0223801 A1 | 11/2004 | Detwiler et al. |
| 2004/0230168 A1 | 11/2004 | Keaty, Jr. et al. |
| 2004/0240927 A1 | 12/2004 | Hoang et al. |
| 2004/0253039 A1 | 12/2004 | Stenton |
| 2004/0265388 A1 | 12/2004 | Zhang et al. |
| 2005/0003178 A1 | 1/2005 | Detert et al. |

(56) References Cited

U.S. PATENT DOCUMENTS

| | | |
|---|---|---|
| 2005/0047845 A1 | 3/2005 | White et al. |
| 2005/0049538 A1 | 3/2005 | Trevillot |
| 2005/0138742 A1 | 6/2005 | Jaszenovics et al. |
| 2005/0175395 A1 | 8/2005 | Quintero et al. |
| 2006/0072962 A1 | 4/2006 | Cybulski et al. |
| 2006/0115520 A1* | 6/2006 | Vanek .................. A61K 31/045 424/443 |
| 2006/0147250 A1 | 7/2006 | Tereschouk |
| 2006/0247568 A1 | 11/2006 | Stenton |
| 2006/0282035 A1 | 12/2006 | Battisti et al. |
| 2007/0020029 A1 | 1/2007 | Baumann et al. |
| 2007/0147946 A1 | 6/2007 | Cybulski et al. |
| 2007/0147947 A1 | 6/2007 | Stenton et al. |
| 2008/0119801 A1 | 5/2008 | Moore |
| 2009/0008021 A1 | 1/2009 | Detert et al. |

FOREIGN PATENT DOCUMENTS

| | | |
|---|---|---|
| CN | 2280607 Y | 5/1998 |
| DE | 2 017 009 A | 10/1971 |
| DE | 44 13 770 A1 | 10/1995 |
| DE | 19860759 | 6/2000 |
| EP | 0 081 816 A2 | 6/1983 |
| EP | 0 232 596 A1 | 8/1987 |
| EP | 0 507 317 A2 | 10/1992 |
| EP | 0 775 641 A1 | 5/1997 |
| EP | 1 721 582 A1 | 11/2006 |
| EP | 1 870 344 A1 | 12/2007 |
| FR | 2 232 923 A5 | 1/1975 |
| FR | 2 776 770 A1 | 10/1999 |
| GB | 2 272 644 A | 5/1994 |
| JP | 1080375 | 3/1989 |
| JP | 7307311 | 11/1995 |
| JP | 9028716 | 2/1997 |
| WO | WO 95/03734 | 2/1995 |
| WO | WO 98/11852 A1 | 3/1998 |
| WO | WO 99/63934 | 12/1999 |
| WO | WO 01/74437 A1 | 10/2001 |
| WO | WO 02/46089 | 6/2002 |
| WO | WO 03/076000 | 9/2003 |
| WO | WO 03/092784 A1 | 11/2003 |
| WO | WO 2004/094494 | 11/2004 |
| WO | WO 2004/110545 A1 | 12/2004 |
| WO | WO 2005/027815 A1 | 3/2005 |
| WO | WO 2005/099808 A1 | 10/2005 |
| WO | WO 2006/055397 | 5/2006 |
| WO | WO 2006/131747 A1 | 12/2006 |
| WO | WO 2008/092200 A1 | 8/2008 |

OTHER PUBLICATIONS

Third Office Action from the State Intellectual Property Office of the People's Republic of China for Chinese Patent Application No. 200980157624.1, dated Jun. 10, 2014.

European Search Report for European Application No. 14187428.9 dated Feb. 3, 2015.

International Search Report re PCT/US2009/069730, Mar. 23, 2010.

* cited by examiner

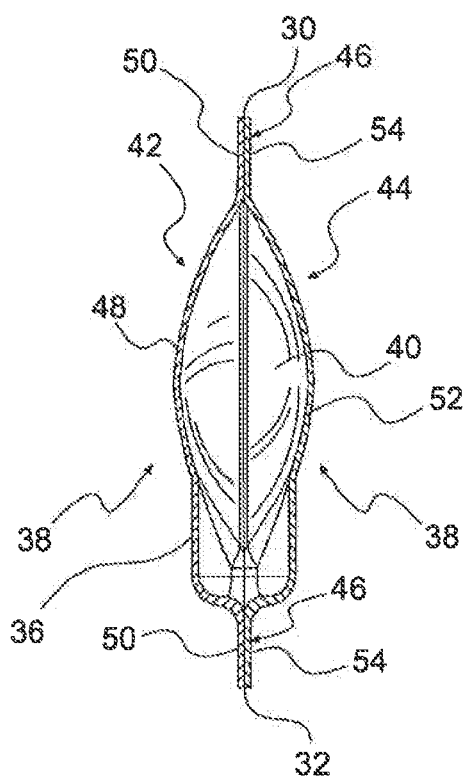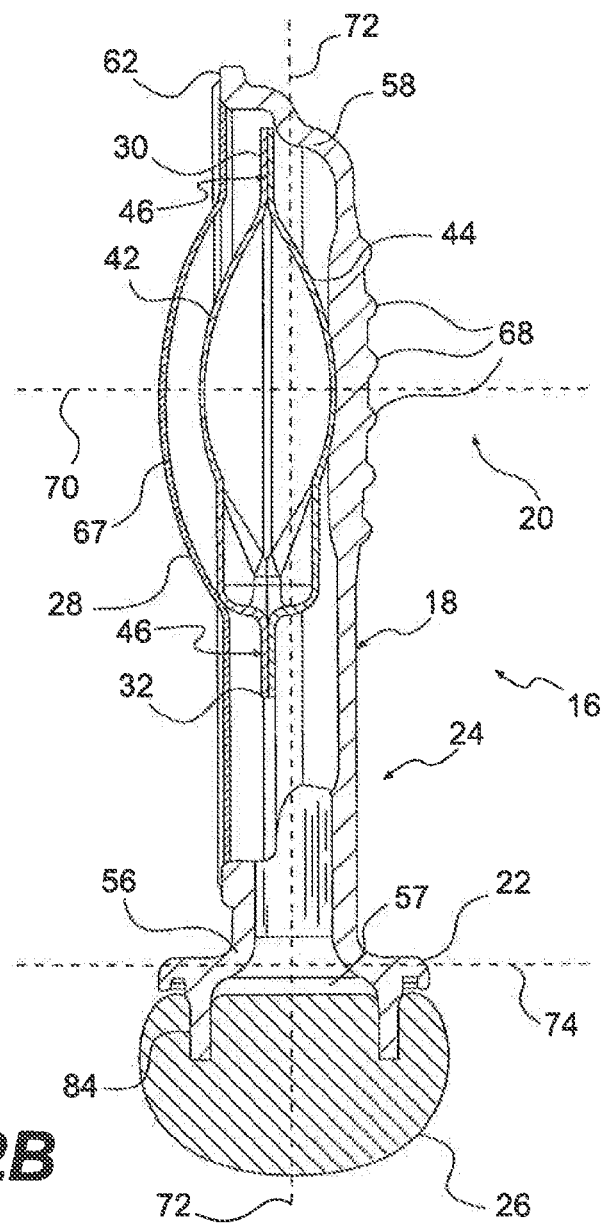

FLUID APPLICATION DEVICE AND METHOD

This is a division of application Ser. No. 12/654,660, filed Dec. 29, 2009 and claims the benefit of U.S. provisional application No. 60/141,540, filed Dec. 30, 2008, both of which are incorporated herein by reference.

FIELD

The present application relates to an apparatus and method for fluid application.

INTRODUCTION

Preparation of patients for various medical procedures, e.g., surgery, typically includes application of a topical solution (or fluid), e.g., an antiseptic solution, to sanitize the area targeted for medical procedures. Topical solutions may be applied to the targeted area by saturating a sponge-like material with the solution and using a handheld device, for example a pair of forceps or a hemostat, to direct the saturated sponge to the targeted area. The sponges or foam materials are typically soaked in a fluid contained within an open pan or other container.

In certain instances, existing devices used to apply solutions exhibit various disadvantages. For example, typical applicators utilize sponges that do not retain fluid efficiently, resulting in leakage. As a result, preparing targeted areas for antiseptic cleaning becomes a messy procedure. In addition, leakage of various fluids onto areas outside of the targeted areas can lead to pooling of the various fluids which may cause irritation, discomfort, and/or other undesirable conditions.

Another example of a disadvantage involves the difficulty of dispensing a desired dose of fluid at the targeted area. During fluid application, in certain instances, it may be desirable to control the amount of fluid, e.g., antiseptic solution, that is dispensed from the applicator. Because existing applicators dispense fluid inefficiently, however, the precise amount of solution delivered to the targeted area may be difficult to determine. This may result in either more or less solution applied to the targeted area than is desired. In addition, typical applicators utilize foams and/or fluid delivery systems that fail to timely dispense a precise amount of fluid. For example, certain applicators with internal ampoules that store fluid take time for the fluid to saturate the sponge and thus be available for application to the patient. This can result in unpredictable and imprecise dispensing of the desired solution.

SUMMARY

In some aspects, the present disclosure is directed to an applicator device for applying a fluid. The applicator device may include a handle having a proximal end and a distal end. The handle may comprise a receptacle at the proximal end of the handle, the receptacle configured to receive a packet containing a fluid and facilitate expulsion of the fluid from the packet. The handle may also comprise a flexible lid configured to sealingly enclose the packet within the receptacle and configured to deflect in response to application of exterior pressure enabling application of the exterior pressure to the packet when disposed within the receptacle to thereby compress the packet to release the fluid from the packet. In addition, the applicator device may include a base at the distal end of the handle. The base may include a distal opening and may be configured to direct flow of the released fluid. The applicator device may also include an applicator pad coupled to the base, in fluid communication with an interior portion of the receptacle, wherein a portion of the pad is inserted within the distal opening of the base, and a portion of the pad is wrapped around an exterior portion of the distal opening of the base.

In certain aspects, the present disclosure is directed to an applicator device for applying a fluid, comprising a handle, a base, and an applicator pad. The handle may include a proximal end and a distal end, and may comprise a receptacle at the proximal end of the handle. The handle may be configured to receive a packet containing a fluid and facilitate expulsion of the fluid from the packet. The applicator device may include at least one venting feature configured to allow air flow into or out of the receptacle. The applicator device may also include a flexible lid configured to sealingly enclose the packet within the receptacle and configured to deflect in response to application of exterior pressure, enabling application of the exterior pressure to the packet when disposed within the receptacle to thereby compress the packet to release the fluid from the packet. The base may be located at the distal end of the handle and may include a distal opening. The base may be configured to direct flow of the released fluid and may include a distal opening in the base. In addition, the applicator pad may be configured to be coupled to the base, in fluid communication with an interior portion of the receptacle via the distal opening in the base.

In some aspects, the present disclosure is directed to a system for applying a fluid. The system may include a packet containing a fluid and comprising first and second opposing packet sides defining therebetween a sealed space containing the fluid. The packet may further comprise a frangible area configured to rupture upon compressing the packet to release the fluid from the packet. The packet may also include a collapsibility feature enabling the first packet side of the packet to invert from a convex position to a concave position upon compressing the packet such that the formerly sealed space is substantially completely collapsed. The system may also include an applicator device comprising a handle and an applicator pad. The handle may include a proximal end and a distal end, and may comprise a receptacle at the proximal end of the handle, the receptacle being configured to receive the packet of the fluid and facilitate expulsion of the fluid from the packet. The handle may also comprise a flexible lid configured to sealingly enclose the packet within the receptacle. The handle may further comprise a base disposed at the distal end of the handle and configured to direct flow of the released fluid. The base may include a distal opening. The applicator pad may be configured to be coupled to the base, in fluid communication with an interior portion of the receptacle via the distal opening of the base.

In certain aspects, the present disclosure is directed to a method for applying a fluid to a surface. The method may include applying pressure to a flexible outer surface of a handle at a proximal end of an applicator device to thereby exert pressure on a fluid-filled packet disposed within the handle to compress a flexible portion of the packet, wherein said pressure may cause a frangible area of the packet to rupture to release the fluid from the packet. In some embodiments of the method, the released fluid may flow through the handle through a distal opening in a base at a distal end of the applicator device to an applicator pad attached to the base. In certain embodiments of the method, the applicator pad may be inserted within the distal opening in the base and wrapped around an outer portion of the distal opening of the base. The method may also include contacting the applicator pad of the applicator device to a surface to transfer the fluid from the applicator pad to the surface.

BRIEF DESCRIPTION OF THE DRAWINGS

FIG. 2A illustrates a cross-sectional side view of a packet for containing fluid, according to certain embodiments;

FIG. 2B illustrates a cross-sectional side view of an assembled applicator system including the packet of FIG. 2A;

DESCRIPTION OF VARIOUS EMBODIMENTS

In this application, the use of the singular includes the plural unless specifically stated otherwise. In this application, the use of "or" means "and/or" unless otherwise stated. Furthermore, the use of the term "including," as well as other forms, such as "includes" or "included," is not limiting. Also, terms such as "element" or "component" encompass both elements and components comprising one unit and elements and components that comprise more than one unit unless specifically stated otherwise.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The disclosed applicator may be configured to dispense/apply any liquid with a viscosity suitable to allow passage through, and dispensing by, the disclosed device. In some embodiments, the disclosed applicator may be utilized to dispense/apply an antiseptic fluid. The term "antiseptic fluid," as used herein, refers to a liquid that, in certain embodiments, may be used to sanitize a region in preparation for various medical procedures.

Reference will now be made in detail to the drawings. Wherever possible, the same reference numbers will be used throughout the drawings to refer to the same or like parts.

Figure 1:
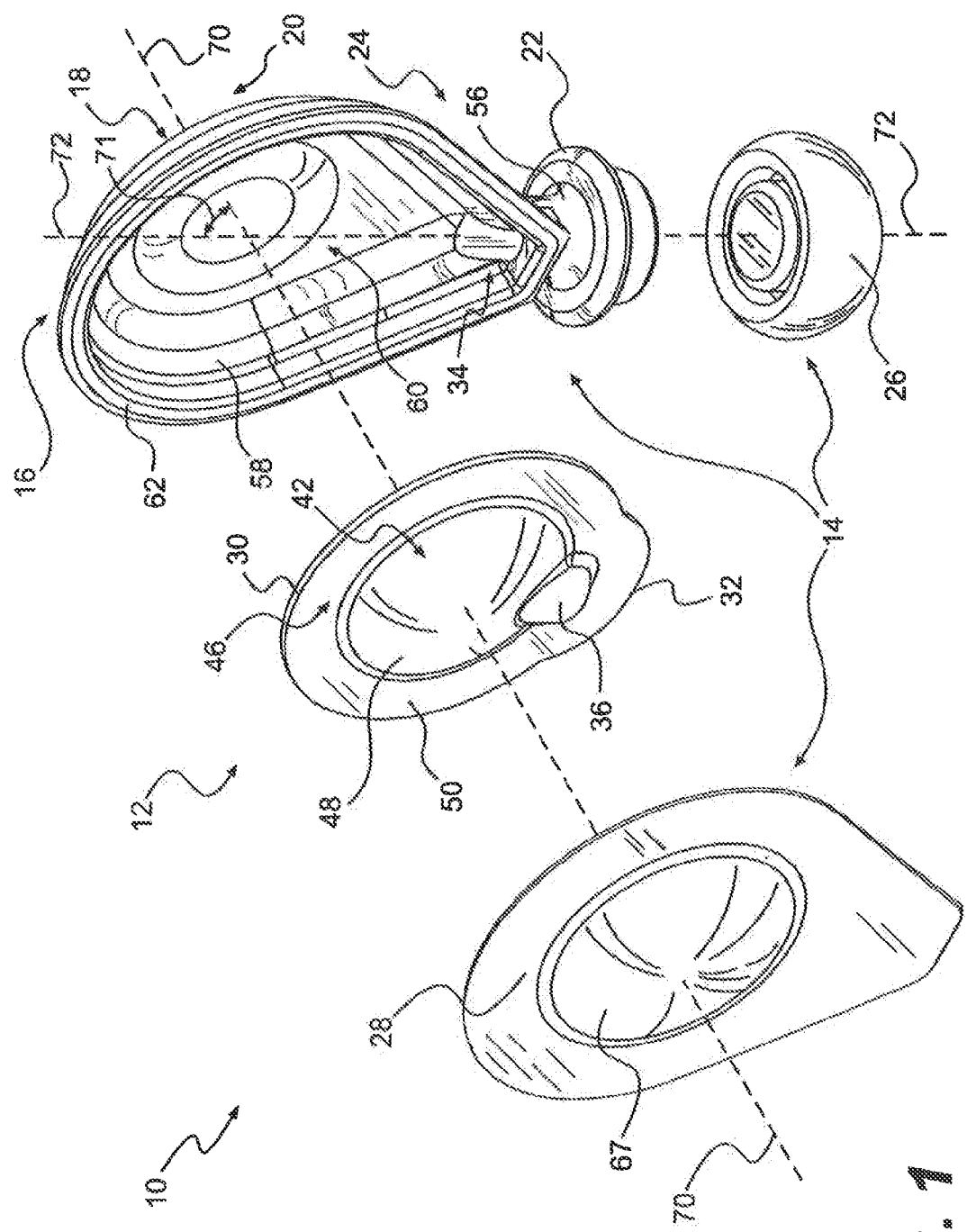
FIG. 1 illustrates an exploded view of an applicator system according to an exemplary disclosed embodiment.

FIG. 1 illustrates an exploded view of a system 10 for applying a fluid. As shown in FIG. 1, system 10 may include a packet 12 configured to contain a fluid. In addition, system 10 may include an applicator device 14 configured to apply a fluid to a surface. Applicator device 14 may include a handle 16. Handle 16 may comprise a receptacle 18 at a proximal end 20 and a base 22 at a distal end 24. Applicator device 14 may also include an applicator pad 26 coupled to base 22. Applicator device 14 may further include a lid 28 configured to enclose packet 12 within receptacle 18.

Packet

Packet 12 may include a proximal end 30 and a distal end 32 and may be configured to be inserted into receptacle 18 with distal end 32 of packet 12 oriented toward distal end 24 of handle 16, as shown in FIG. 1. The fluid within packet 12 may be expelled by applying an external force to packet 12, which may cause packet 12 to burst (e.g., at a frangible area), allowing (or forcing) the fluid to flow distally, through base 22 and into applicator pad 26.

Packet 12 may be formed in any suitable shape. In some embodiments, packet 12 may have a substantially round shape, as shown in the accompanying drawings. Packet 12 may be configured to fit within, and correspond generally to, the shape of receptacle 18, which may also be substantially round, as shown. In some embodiments, packet 12 may contain orienting features to simplify assembly of the components of fluid application system 10. For example, packet 12 may have a shape that corresponds to a mating shape of receptacle 18. In some embodiments, the mating shapes may be asymmetrical to orient packet 12 with respect to receptacle 18.

In certain embodiments wherein packet 12 and receptacle 18 have mating substantially round shapes (e.g., as shown in FIG. 1), the orienting features may include a structure on receptacle 18 that deviates from the substantially round shape of receptacle 18 and a corresponding structure on packet 12 that deviates from the substantially round shape of packet 12. For example, the orienting features may include asymmetrical shapes, such as corresponding protrusions on receptacle 18 and packet 12 (forming a teardrop-type shape), as shown in FIG. 1. That is, in some embodiments, applicator device 14 may include a packet protrusion 36 on packet 12, which is configured to orient with corresponding receptacle feature 34 on receptacle 18.

Mating, asymmetrical shapes, such as teardrops, may not only facilitate assembly by making it readily apparent how packet 12 and receptacle 18 should be aligned with one another, but may also ensure that the frangible area of packet 12 is oriented toward the distal end of applicator device 14 so that fluid released from packet 12 may readily flow to applicator pad 26. For example, in certain embodiments, receptacle 18 may be configured to orient packet 12 with packet protrusion 36 positioned toward base 22. In such embodiments, packet protrusion 36 may include the frangible area of packet 12. This positioning of the frangible area (i.e., toward base 22) may allow fluid to readily flow, upon rupture of the frangible area, from packet 12 toward (and through) base 22 and into applicator pad 26, e.g., due to gravity and/or due to squeezing of packet 12 to expel the fluid from packet 12 and receptacle 18.

As shown in FIG. 2A, packet 12 may include opposing sides 38, defining therebetween a sealed space 40, which may be fluid-filled. Either or both of opposing sides 38 may be deformable. The fluid within packet 12 may be expelled by applying an external force to opposing sides 38 of packet 12, which may cause packet 12 to burst, allowing (or forcing) the fluid to flow distally, through base 22 and into applicator pad 26.

The frangible area of packet 12 may be configured to break open upon application of a reasonable activation force (e.g., by squeezing/compressing packet 12). Although the frangible area may be configured to break open upon application of force by a user, packet 12, including the frangible area, may be configured to maintain structural integrity during handling, storage, etc., in order to prevent leakage or accidental opening.

Packet 12 may be formed of any type of material that is suitable for forming a fluid-holding packet with a frangible area. For purposes of this disclosure, the term "frangible" shall mean breakable, burstable (as in the case of a flexible packet), or otherwise configured to rupture. In some embodiments, the frangible area may be a part of the packet that has been prepared to have less strength than other portions of the packet. For example, in certain embodiments, a frangible seal may be created by sealing the area desired to be frangible at a lower temperature than required for maximum seal strength. In other embodiments, a frangible seal may be created by forming the frangible area using a specially formulated "peel-able" film that has inherently lower adhesion.

Figure 2C:
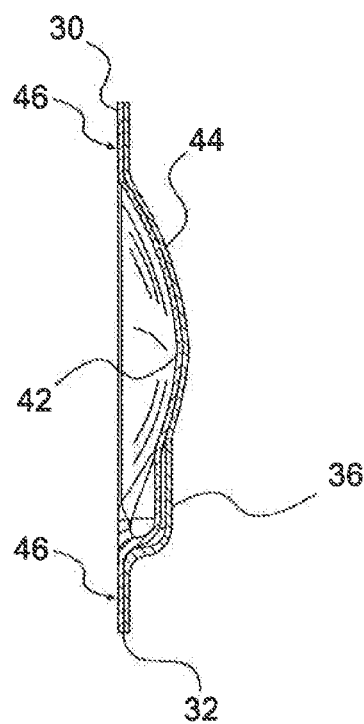
FIG. 2C illustrates a cross-sectional side view of the packet of FIG. 2A in a collapsed state.
Figure 2D:
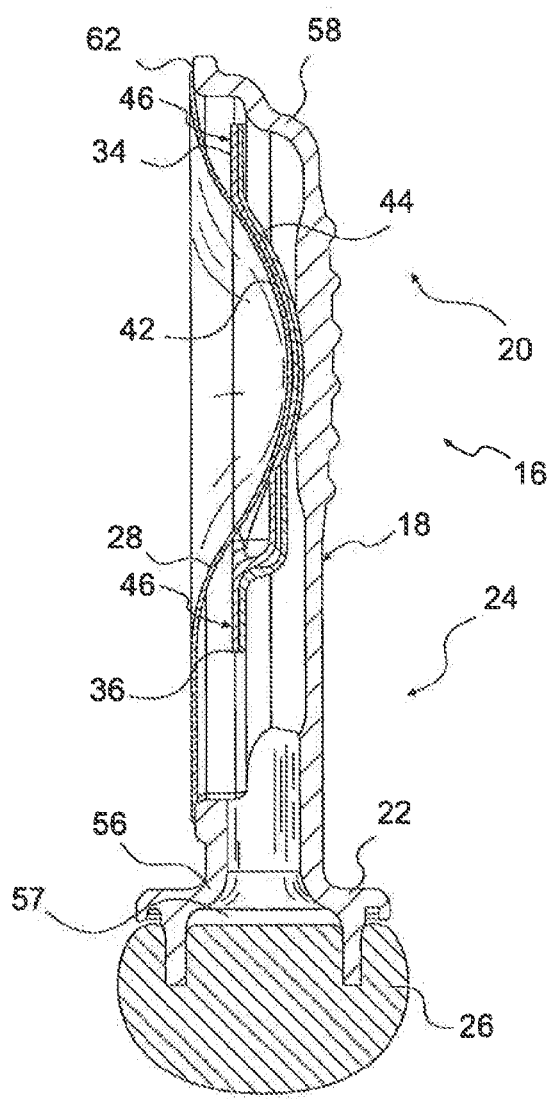
FIG. 2D illustrates a cross-sectional side view of an assembled applicator system including a collapsed packet.

Packet 12 may be self-draining by way of a two-sided configuration that allows one side to invert smoothly into the other when packet 12 is compressed. For example, as shown in FIGS. 2A and 2B, packet 12 may include a first packet side 42 and a second packet side 44. First packet side 42 and second packet side 44 may be sealed together at a sealed portion 46 about the perimeter of packet 12. Packet 12 may be configured so that, upon compression, first packet side 42 inverts into second packet side 44, thus collapsing sealed space 40, as shown in FIGS. 2C and 2D. Packet 12 may be configured to completely collapse, (and, in some embodiments, remain collapsed), in order to evacuate substantially all fluid from packet 12.

Packet 12 may include a collapsibility feature enabling first packet side 42 of packet 12 to invert from a convex position, as shown in FIGS. 2A and 2B, to a concave position, as shown in FIGS. 2C and 2D, upon compressing packet 12 so that the formerly sealed space 40 is substantially completely collapsed. In some embodiments, first packet side 42 and second packet side 44 of packet 12 may be formed from films of differing thicknesses. For example, in some embodiments, first packet side 42 may be formed of a thinner film than second packet side 44 to enable the deformation of first packet side 42 to effectuate inversion of first packet side 42 and thereby the collapse of packet 12.

Alternatively or additionally, first packet side 42 may be sized and/or shaped differently than second packet side 44 to provide the collapsibility of packet 12. For example, in some embodiments, first packet side 42 may include a first central portion 48 and first peripheral portions 50, and second packet side 44 may include a second central portion 52 and second peripheral portions 54. First packet side 42 and second packet side 44 may be sealed to each other at a junction between first peripheral portions 50 and second peripheral portions 54. In certain embodiments, first central portion 48 may have a smaller diameter (e.g., on the order of tenths or hundredths of an inch) than second central portion 52, thereby forming a collapsibility feature, allowing first packet side 42 to nest within second packet side 44, as shown in FIGS. 2C and 2D.

In certain embodiments, the liquid contained in packet 12 may be an antiseptic solution containing an active ingredient. Various antiseptic solution active ingredients are known in the art, including, but not limited to, ethanol, isopropyl alcohol, other alcohols, and combinations thereof; benzalkonium chloride; benzethonium chloride; chlorhexidine gluconate; chlorhexidine gluconate with alcohol; chloroxylenol; cloflucarban; fluorosalan; hexachlorophene; hexylresorcinols; iodine-containing compounds; povidone iodine; povidone iodine with alcohol, ethanol, isopropyl alcohol and other alcohols, and combinations thereof.

In some embodiments, the antiseptic solution may include a biguanide derivative and/or salts thereof, e.g., olanexidine [1-(3,4-dichlorobenzyl)-5-octylbiguanide] and salts thereof, as the active ingredient, as disclosed, for example in U.S. Pat. No. 5,376,686. In certain embodiments, the topical antiseptic may include olanexidine gluconate.

The antiseptic solution may also incorporate certain surfactants, for example, polyoxyethylene-based nonionic surfactants, and/or alcohols, for example, ethanol, isopropyl alcohol and other alcohols, and/or water, in varying amounts. Useful surfactants are known to one skilled in the art, for example, Poloxamer 124 (a/k/a Polyoxypropylene-polyoxyethylene Block Copolymer 124), which is available as Polyoxyethylene(20) polyoxypropylene(20) glycol from Asahi Denka Co., Ltd., Japan, POE (9) lauryl ether (available as 'BL-9EX' from Nikko Chemicals Co., Ltd., Tokyo, Japan), POE (10) lauryl ether, also known as nonoxynol-10, or NP-10, (available as 'Emulin NL-100' from Sanyo Chemical Industries, Ltd., Kyoto Japan).

In certain embodiments, the antiseptic solution may include an active ingredient and a polyoxyethylene-based nonionic surfactant in various concentrations. In some embodiments, the polyoxyethylene-based nonionic surfactant may be present at a concentration of about 0.05 to about 16% (w/v).

In certain embodiments, the topical antiseptic may include a biguanide derivative, and/or salts thereof, in a concentration of about 0.05 to about 5.0% (w/v of biguanide base), in some embodiments, the biguanide derivative or salt thereof may be olanexidine [1-(3,4-dichlorobenzyl)-5-octylbiguanide] or a salt thereof.

Figure 4A:
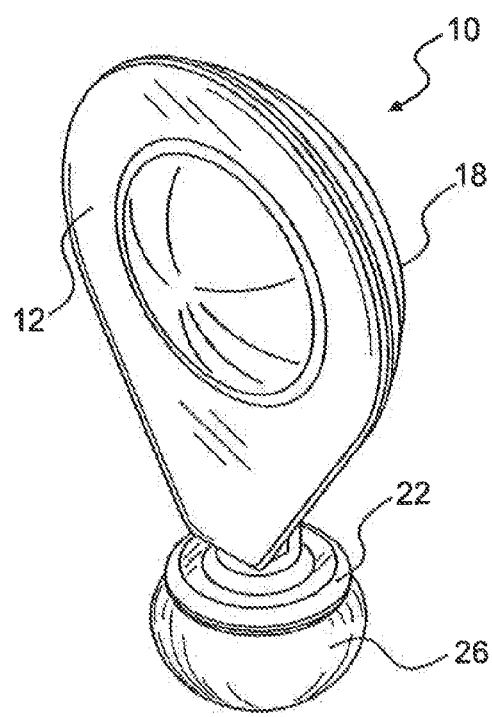
FIG. 4A illustrates a perspective front view of an assembled applicator system, according to certain embodiments.

In some embodiments of system 10, applicator device 14 may be provided in ready to use form. For example, applicator device 14 may be stored, packaged, and/or shipped, etc. with applicator pad 26 attached to base 22 and with packet 12 enclosed within receptacle 18 by lid 28, as shown in FIG. 2B, (See also FIG. 4A.) In such embodiments, packet 12 may be pre-filled with a fluid, such as an antiseptic fluid, for example.

Receptacle

Receptacle 18 may be configured to receive packet 12 and facilitate expulsion of the fluid from packet 12. Handle 16 may have features that facilitate the delivery of fluid to absorbent pad 26, such as a smooth and tapered neck 56 between receptacle 18 and base 22, which may include a distal opening 57 through which the fluid may flow from receptacle 18 to applicator pad 26, as shown in FIGS. 2B and 2D. Receptacle 18 may comprise a bowl-like shell 58 defining a recess 60, and having a rim 62. (See FIG. 1.) Lid 28 may be sealingly attached to rim 62, e.g., using an heat sealing, radio frequency (RF) welding, adhesive bonding, laser welding, or any other suitable type of fixation. In some embodiments, receptacle 18 may include energy directors or textured surfaces for ultrasonic welding or otherwise joining lid 28 to receptacle 18.

In addition to packet-orienting features such as asymmetrical shapes, as described above, receptacle 18 may include one or more other packet-orienting features such as, but not limited to, a depression, a well, ribs, an emboss, a debris or a series of such elements, to accept and/or secure packet 12. For example, as shown in FIGS. 2B and 2D, receptacle 18 may include various steps and/or contours that may be shaped to mate with, and/or retain corresponding features on, packet 12. (See also, FIG. 1.)

Figure 3A:
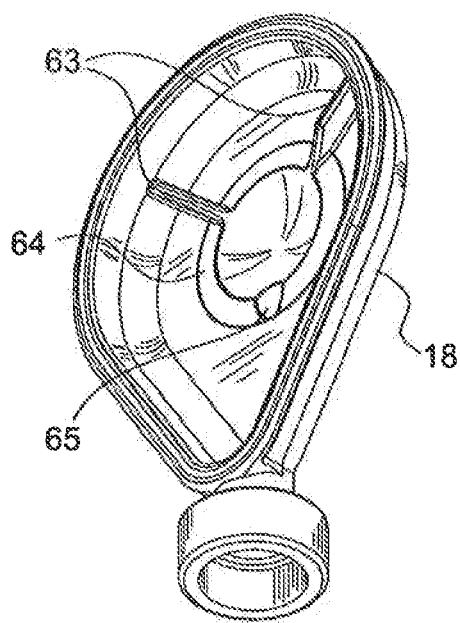
FIG. 3A is a perspective view of a handle with a receptacle of an applicator device according to an exemplary disclosed embodiment.
Figure 3B:
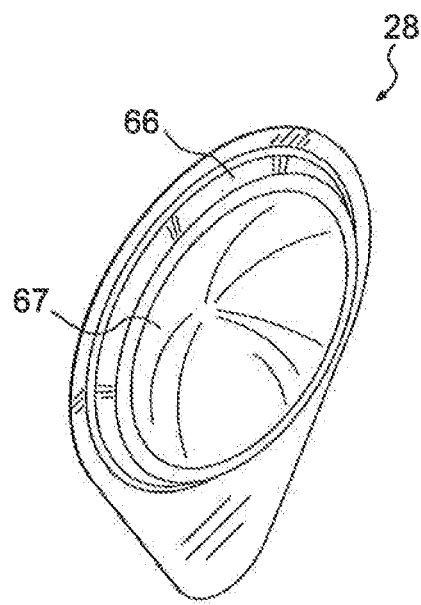
FIG. 3B is a perspective view of a lid corresponding to the receptacle shown in FIG. 3A.
Figure 3C:
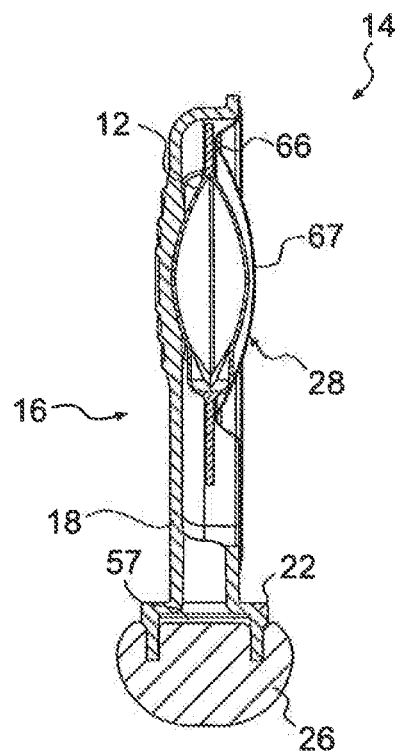
FIG. 3C is a cross-sectional view of an assembled applicator system, according to certain embodiments.

FIGS. 3A-3C illustrate an embodiment of applicator device 14 including exemplary packet-orienting features. For example, as shown in FIG. 3A, receptacle 18 may include one or more inner ribs 63, an embossed ridge 64, and a de-bossed area forming a well 65. As shown in FIG. 3B, lid 28 may be configured to be used with the receptacle shown in FIG. 3A. In some embodiments, lid 28 may include an indented face 66 which may allow a lid dome 67 of lid 28 to have a lower profile, as shown in FIG. 38, FIG. 3C is a cross-sectional view of an assembled applicator device 14 including the components shown in FIGS. 3A and 3B.

Figure 4B:
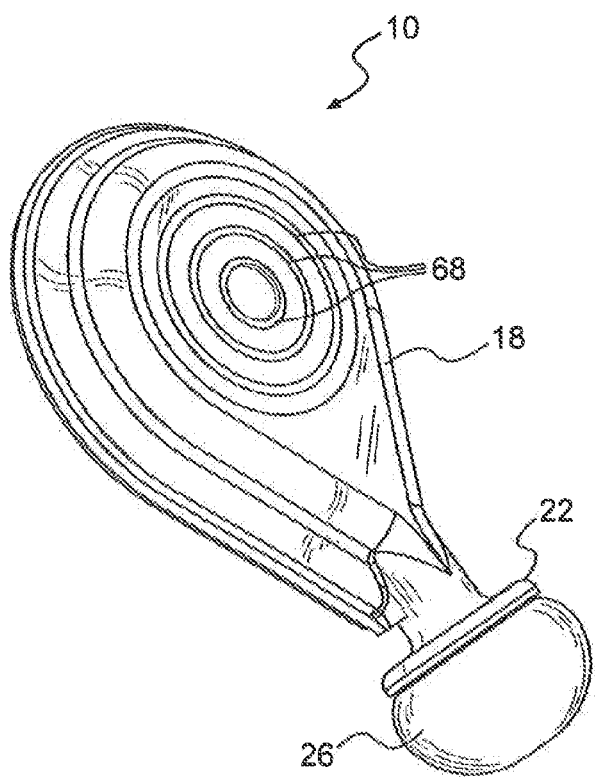
FIG. 4B illustrates a perspective back view of an assembled applicator system, according to certain embodiments.

In addition to orienting features, handle 16 may also include one or ore exterior gripping features to facilitate manipulation of applicator device 14 by a user. For example, receptacle 18 may include gripping features such as ergonomic shaping and/or sizing, as well as indentations, protruding gripping members, textured strips and/or areas, rubberized material, etc., to promote secure gripping of receptacle 18. In some embodiments, handle 16 may include one or more gripping ribs 68 (e.g., on receptacle 18), as shown in FIG. 4B.

In some embodiments, applicator device 14 may include a venting feature configured to allow air flow into or out of receptacle 18. Such a venting feature may be configured to limit fluid leaking out of handle 16 in undesirable locations, while still allowing for a controlled fluid delivery to the absorbent pad. For example, in some embodiments, a venting feature may be located at proximal end 20 of handle 16, where air can pass in and out of handle 16 while the fluid resides at a distal end of handle 16, while applicator device 14 is held upright. In some embodiments, the venting feature may include an area that is left unsealed at a junction between lid 28 and rim 62 of receptacle 18. For example, in certain embodiments, rim 62 of receptacle 18 may include a groove (not shown) over which lid 28 may be left unsealed.

In some embodiments, one or more portions/components of applicator device 14 may be formed of a transparent or translucent material. For example, one or more portions of receptacle 18 may be formed of a transparent or translucent material. In some embodiments, one or more portions of lid 28, packet 12, and/or base 22 may be formed of transparent or translucent material. Transparency and/or translucency of certain portions/components of applicator device 14 may enable observation of the quantity of fluid remaining in packet 12 and/or may facilitate monitoring the flow of the fluid through applicator device 14 while it is being dispensed.

Figure 5A:
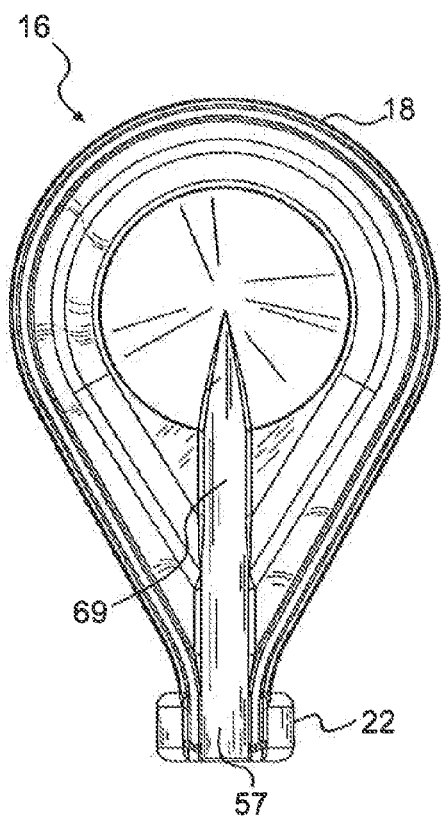
FIG. 5A illustrates a front view of a handle for an applicator device according to certain embodiments.
Figure 6A:
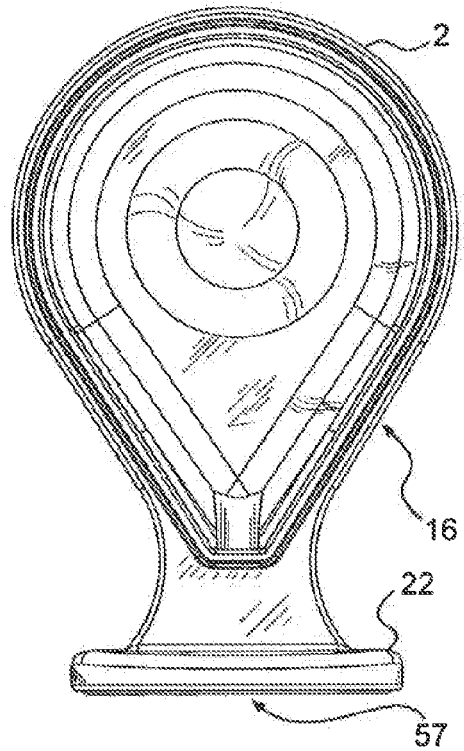
FIG. 6A illustrates a front view of a handle for an applicator device according to certain embodiments.
Figure 5B:
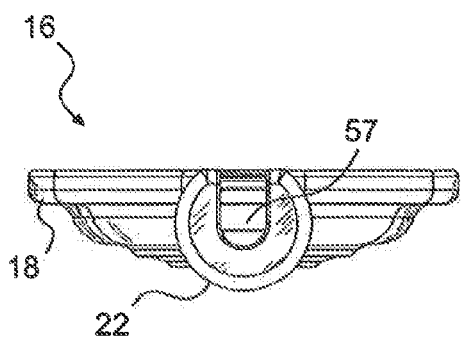
FIG. 5B illustrates a bottom view of a handle for the applicator device shown in FIG. 5A.
Figure 6B:
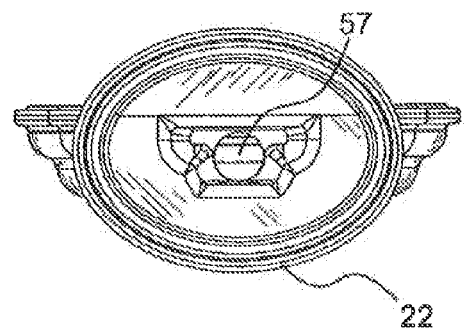
FIG. 6B illustrates a bottom view of a handle for the applicator device shown in FIG. 6A.
Figure 7A:
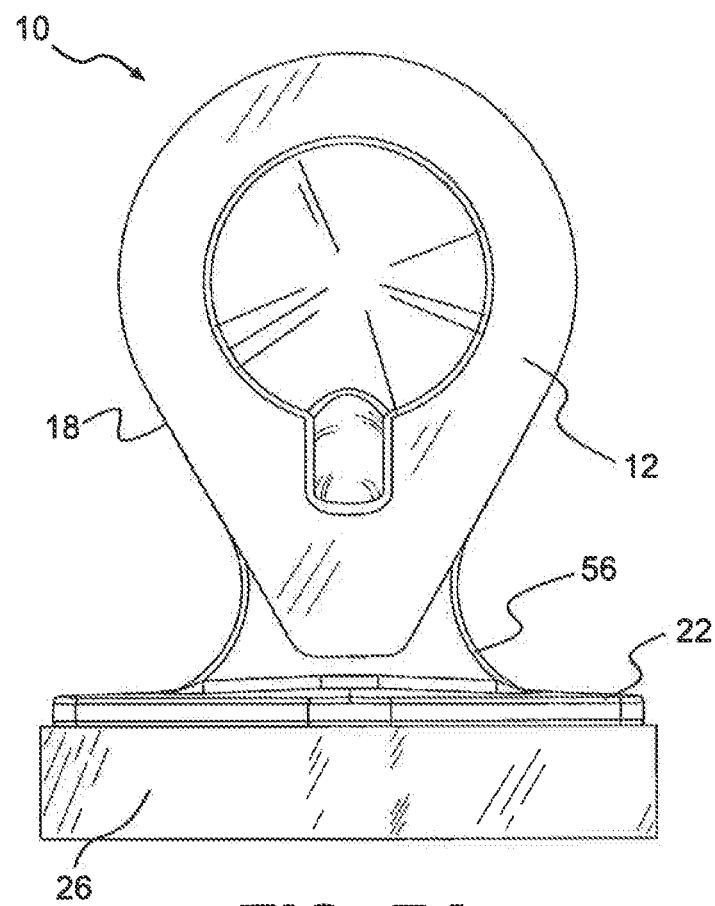
FIG. 7A illustrates a front view of an assembled applicator system, according to certain embodiments.
Figure 7B:
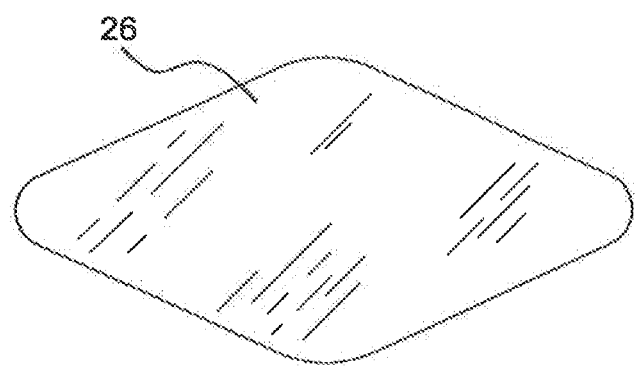
FIG. 7B illustrates a bottom view of the applicator system shown in FIG. 7A.

As shown in FIGS. 5A and 5B, in some embodiments, receptacle 18 may include a three-sided channel 69 configured to direct flow of the fluid to distal opening 57 in base 22, which may be slotted to incorporate channel 69. Also, as shown in FIGS. 6A and 6B, handle 16 can have a wider base 22 with a flared distal opening 57. Such a wider base 22 may be compatible with a wider applicator pad 26. For example, as shown in FIGS. 7A and 7B, applicator device 14 may include a wider base 22 and a corresponding wider applicator pad 26. Features such as channel 69, a flared-type distal opening 57, and a wider base 22 may facilitate increased flow and/or distribution of fluid to applicator pad 26.

Handle 16, i.e., receptacle 18 and base 22 may be formed using any suitable process, such as injection molding, machining, and/or any other suitable manufacturing methods. Features such as open channel 69 and/or flared-type distal opening 57 may facilitate molding of handle 16. Handle 16 may be formed of any suitable material, including, for example, thermoplastics such as polyester, S-B block copolymer, polyolefins, etc.

Lid

Lid 28 may be configured to sealingly enclose packet 12 within receptacle 18. Lid 28 may also be flexible, and thus, configured to deflect in response to application of exterior pressure, enabling application of the exterior pressure to packet 12 when disposed within receptacle 18 to thereby compress packet 12 to release the fluid from packet 12. In some embodiments, lid 28 may be configured to distribute force applied to lid 28. For example, in some embodiments, lid 28 may have a dome shape, as illustrated by lid dome 67. (See FIGS. 1, 2B, and 3B.)

Lid 28 may be formed by any suitable method, including thermoforming and die cutting for semirigid embodiments of lid 28. For embodiments wherein lid 28 may be a stretchable material, lid 28 may be die cut stretched. Exemplary materials from which lid 28 may be formed include any materials suitable for sealing to receptacle 18. Such materials may include, for example, polyesters, polyolefins, S-B block copolymers, etc.

Lid 28 may be sealingly attached to receptacle 18 using any suitable method. For example, lid 28 may be attached to receptacle 18 using heat sealing, adhesive/glue, laser welding, ultrasonic welding, etc.

Base

Base 22 may be located at distal end 24 of handle 16 and may be configured to direct flow of fluid released from packet 12 to applicator pad 26. As shown in FIG. 2B, distal opening 57 may enable the fluid to flow to applicator pad 26 after being released from packet 12. As described in more detail below, in some embodiments, distal opening 57 may be configured to receive a portion of applicator pad 26.

Base 22 may be formed in a variety of shapes and sizes. In some embodiments, the shape and/or size of base 22 may generally correspond to that of applicator pad 26, as shown in FIGS. 6A and 6B, (See also FIG. 1.) In other embodiments, applicator pad 26 may have a shape and/or size that differs from that of base 22.

Base 22 may be oriented at an angle relative to receptacle 18. For example, certain embodiments of receptacle 18, e.g., embodiments having a substantially round shape, as in FIG. 1, may be formed about a central receptacle axis 70 through, e.g., the substantially round shape of receptacle 18. Central receptacle axis 70 may be oriented at an angle 71 relative to an axis 72 perpendicular to a plane 74 (see FIG. 2B) including base 22. In some embodiments, angle 71 may be approximately 90 degrees, as shown in FIGS. 1 and 2B, for example. In other embodiments, angle 71 may be any angle within the range of 0 to 180 degrees. For example, in FIG. 8, angle 71 is shown at approximately 45 degrees.

Figure 8:
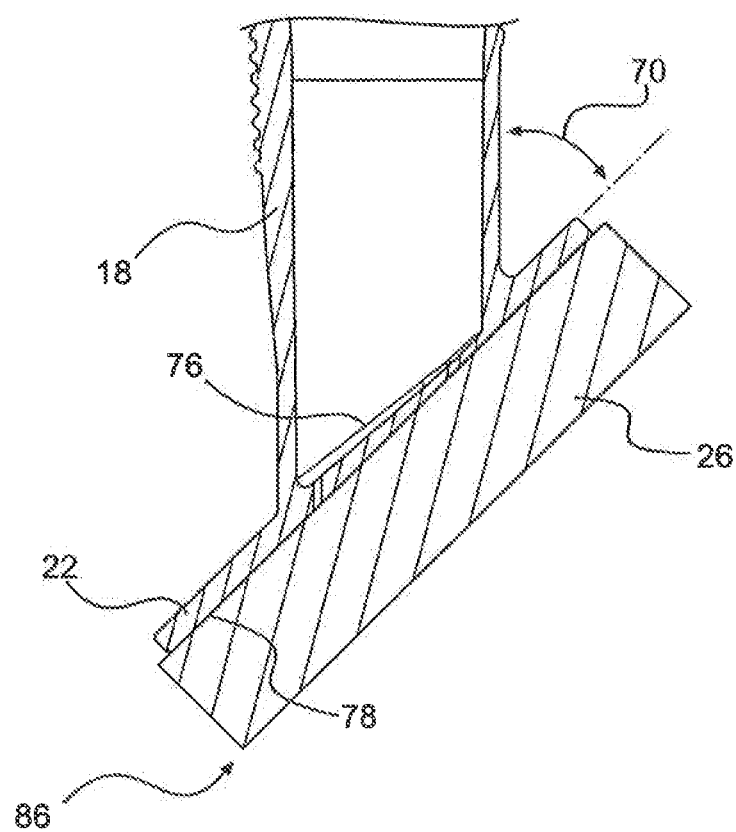
FIG. 8 illustrates a cross-sectional side view of a portion of an applicator device, according to certain embodiments.

As shown in FIG. 8, base 22 may include an inner surface 76 and an outer surface 78 to which applicator pad 26 may be configured to be affixed. In some embodiments, as shown in FIGS. 9A-9H, base 22 may include one or more perforations 80 over which applicator pad 26 may be configured to be affixed. Perforations 80 may allow flow of the fluid from receptacle 18 to applicator pad 26.

Figure 9A:
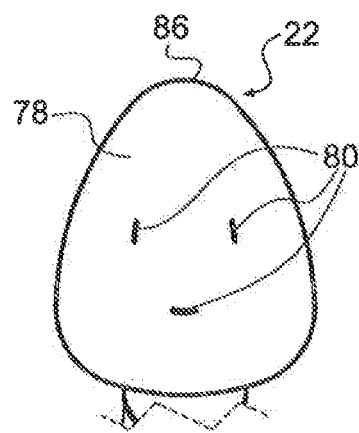
FIGS. 9A-9H illustrate several exemplary disclosed embodiments of a base of an applicator device.
Figure 9B:
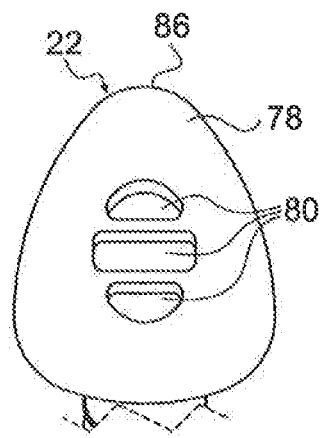
Figure 9C:
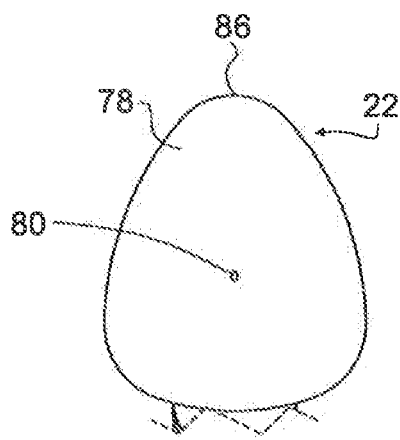
Figure 9D:
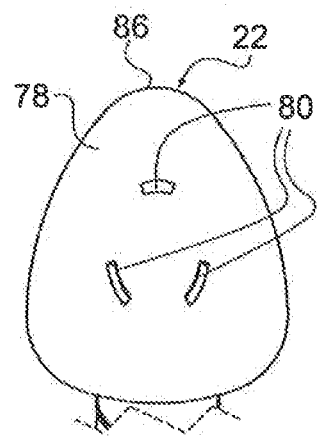
Figure 9E:
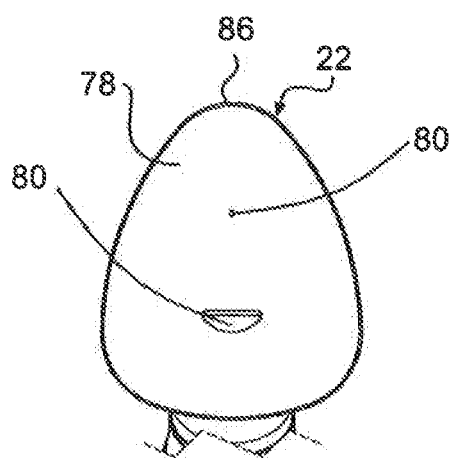
Figure 9F:
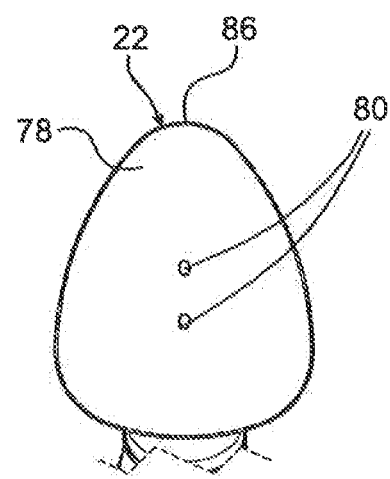
Figure 9G:
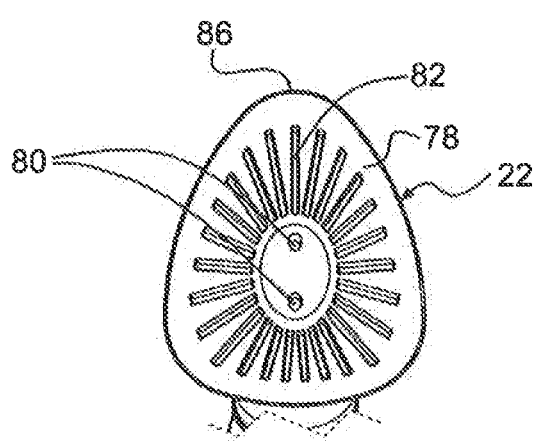
Figure 9H:
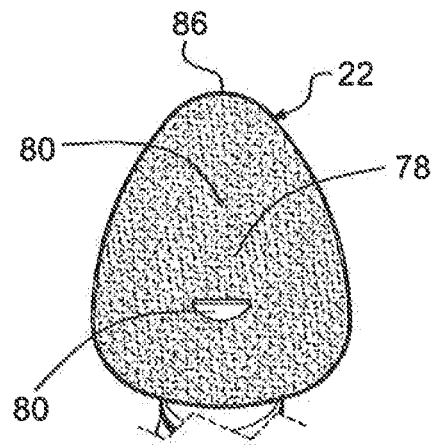

In some embodiments, outer surface 78 may include one or more channels 82, as shown in FIG. 9G. Channels 82 may be configured to distribute the fluid to different portions of applicator pad 26. Also, in some embodiments, outer surface 78 of base 22 may be textured, as shown in FIG. 9H. Texture may not only promote attachment of applicator pad 26 to base 22, but also may facilitate distribution of fluid to different parts of applicator pad 26.

According to certain embodiments, base 22 may couple to receptacle 18. Base 22 may couple to receptacle 18 in a variety of ways known in the mechanical arts, including, but not limited to, attachment by hinges, adhesives, mechanical interlocks, threaded portions, press-fits, friction-fits, interference fits, slide-fits, and/or combinations thereof. According to other embodiments, base 22 may be integrally formed with receptacle 18. An integral base/handle combination may be manufactured by various processes known in the art, including, but not limited to, molding, injection molding, casting, machining, or combinations thereof.

In certain embodiments, applicator device 10 may include an interchangeable attachment between receptacle 18 and base 22. An interchangeable attachment may, for example, facilitate the use of bases having various shapes and sizes on the same receptacle 18, and vice versa. This may facilitate, e.g., the use of differently-sized applicator pads with the same receptacle 18.

Applicator Pad

Applicator pad 26 may be configured to be coupled to base 22, in fluid communication with an inner portion of receptacle 18. In some embodiments, as shown in FIG. 2B, a portion of applicator pad 26 may be inserted into distal opening 57 in base 22 and wrapped around an outer portion 84 of distal opening 57. Applicator pad 26 may be attached to base 22 (e.g., via ultrasonic welding, adhesive, etc.) on outer portion 84 of distal opening 57. In some wrap-around embodiments of applicator pad 26 (e.g., as shown in FIG. 2B), applicator pad 26 may be at least partially preformed, e.g., in a shape such as that shown in FIG. 1. For example, applicator pad 26 may be molded, cut or shaped, and/or compressed into such a configuration.

Figure 10A:
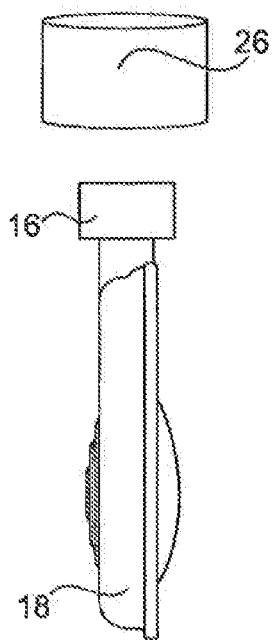
FIGS. 10A-10F depict a series of steps for creating a rounded applicator pad from a flat disk of absorbent pad material.
Figure 10B:
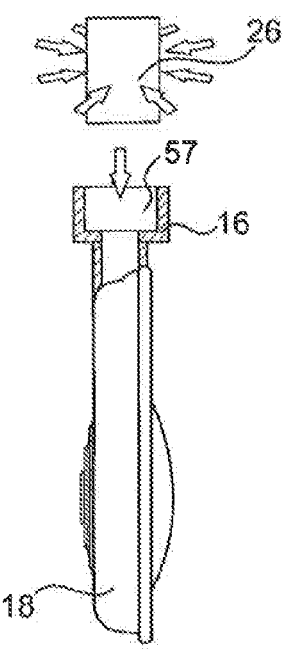
Figure 10C:
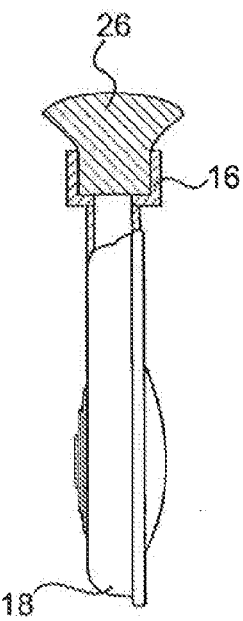
Figure 10D:
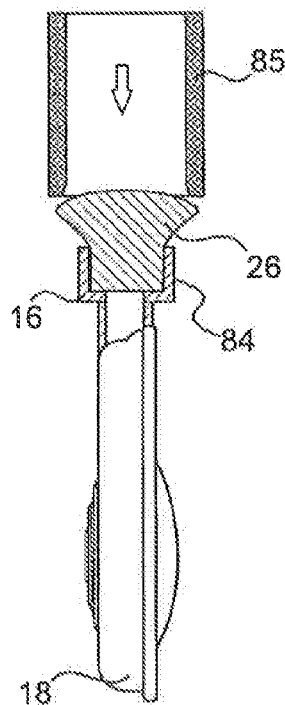
Figure 10E:
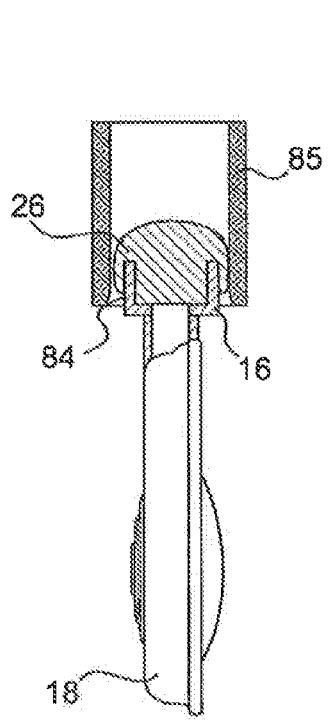
Figure 10F:
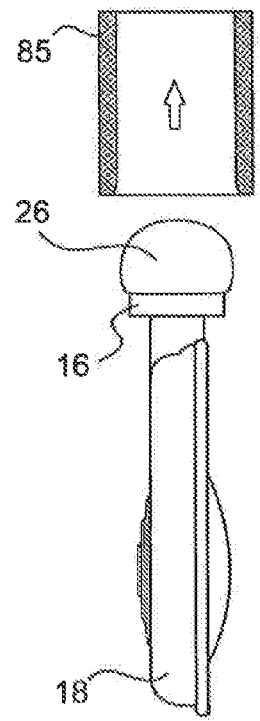

Some wrap-around embodiments of applicator pad 26 may be formed from a disc-shaped pad by inserting a portion of the disc into distal opening 57 in base 22 and then wrapping another portion of the disc around outer portion 84 of distal opening 57. FIGS. 10A-10F depict a series of steps for creating a rounded applicator pad from a flat disk of absorbent pad material. FIG. 10A shows an applicator pad 26 as a flat disk in position over applicator device 14. As shown in FIG. 10B, the disk-shaped applicator pad 26 may be compressed and pressed into distal opening 57 in base 16. FIG. 10C shows the unconstrained disk in distal opening 57. As shown in FIG. 10D, a tool 85 may then be moved down over the disk. FIG. 10E shows the applicator pad 26 having been pushed around the outer portion 84 of distal opening 57, where applicator pad 26 may be affixed to base 16. FIG. 10F shows tool 85 being withdrawn, leaving the finished rounded applicator pad 26.

As noted above, like base 22, applicator pad 26 may have any suitable shape and/or size. In certain embodiments, applicator pad 26 may have a rounded or substantially spherical or hemispherical shape, as shown in FIGS. 1 and 2B, for example. In some embodiments, applicator pad 26 may have alternative shapes, as shown in FIGS. 7A and 7B, as well as FIGS. 8, 9A-9H, and 12A-12D. In certain embodiments, base 22 and/or applicator pad 26 may be generally triangular with rounded edges, as shown in FIGS. 9A-9H and 12A-12D. This generally triangular shape may approximate a teardrop shape, as shown. Other exemplary shapes for base 22 may include, without limitation, rectangular, circular, oval, diamond, various polygonal shapes (see, e.g., FIGS. 7A and 7B), and/or complex shapes comprising combinations thereof.

A generally triangular/teardrop shape or diamond shape may enable applicator device 14 to be used on surfaces having a variety of contours. For example, the smaller tips at the corners of the triangle or, for example, a diamond shape (see, e.g., FIGS. 7A and 7B), particularly the distalmost tip 86, may enable access to crevices and smaller surface features, while the broad, proximal end of applicator pad 26 may provide a large pad surface to enable application of fluid to larger, more gently contoured surfaces.

Applicator pad 26 may couple to base 22 using any of a variety of attachment mechanisms. For instance, applicator pad 26 may be attached to base 22 using any suitable method, including, for example, adhesive bonding using, for example, medical grade cyanoacrylate, UV cure adhesive, and the like. In some embodiments, applicator pad 26 may be attached to base 22 using RF welding, heat staking, ultrasonic welding, laser welding, mechanical interlocks, hook-and-loop mechanisms (e.g., Velcro®), threaded pieces, etc., as well as combinations of these mechanisms. Accordingly, base 22 and applicator pad 26 may each be configured for attachment to one another using any of these mechanisms and, therefore, may include the appropriate features (e.g., texture, adhesive, mechanical latching/clamping elements, coatings, etc) to enable such attachment.

Figure 11:
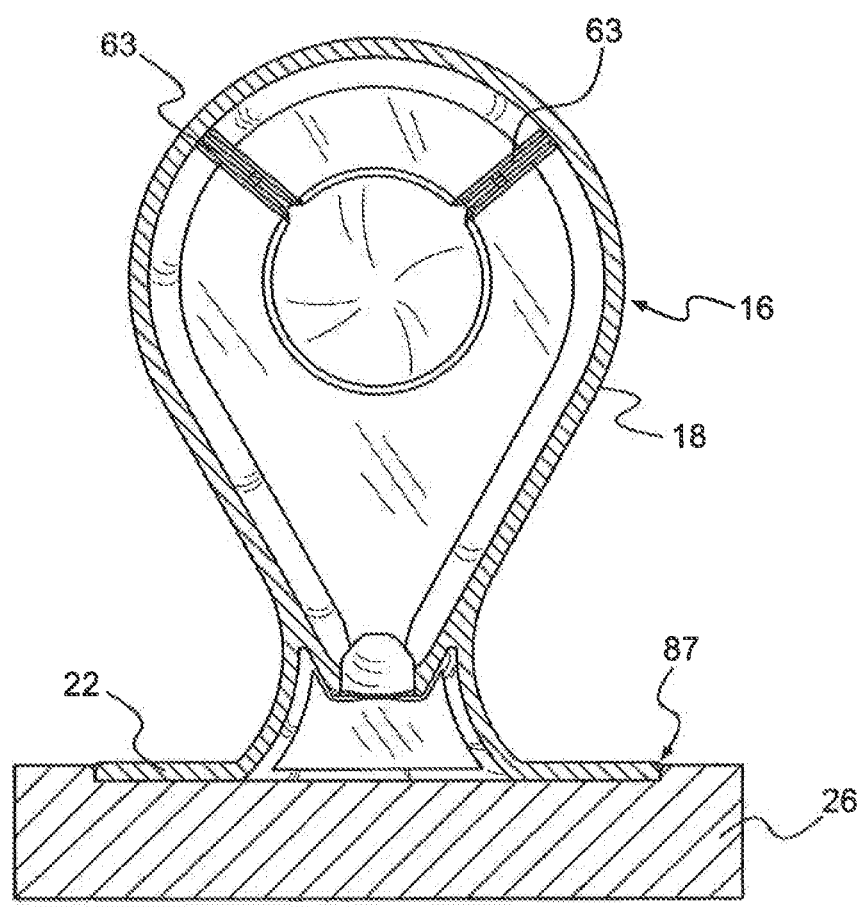
FIG. 11 illustrates an edge weld between an applicator pad and base of an applicator device according to an exemplary disclosed embodiment.

In some embodiments, applicator pad 22 may be attached to base 22 using an edge weld 87, as shown in FIG. 11. Edge weld 87 may be created by holding handle 16 in a fixture with base 22 facing up, placing applicator pad 26 on top of base 22, and bringing the ultrasonic horn down over both applicator pad 26 and base 22. In this way, applicator pad 26 may be wrapped substantially evenly around base 22. During this process, the ultrasonic energy welds the surface of applicator pad 26 to the edge of base 22 and when the ultrasonic horn is withdrawn, the main body of the foam springs back to an uncompressed state.

In some embodiments, applicator pad 26 may include a substantially hydrophobic foam. Alternatively or additionally, applicator pad 26 may include a substantially hydrophilic foam. The term "substantially hydrophobic foam," as used herein, refers to a polymer-based foam that does not absorb a substantial amount of water. In contrast, a definition of a substantially hydrophilic foam is provided below. For purposes of this disclosure, a substantially hydrophobic foam shall refer to any foam that is not substantially hydrophilic, as defined below.

The term "substantially hydrophilic foam," as used herein, refers to a polymer-based foam that has an affinity for water. For example, certain embodiments of the invention can utilize a polyurethane foam with an open-cell pore structure. In certain instances, the substantially hydrophilic foam can be designed for a high rate of fluid absorption such as, for example, absorption of around 20 times the weight of the foam. While not wishing to be bound by theory, a substantially hydrophilic foam can demonstrate an affinity for water through one or more mechanisms including, but not limited to, the presence of polar groups in the polymer chains that can form hydrogen bonds with water or liquids containing active protons and/or hydroxyl groups, a fine open-cell pore structure that channels liquid into the body of the foam structure by capillary forces, and/or the addition of absorbing materials, such as super absorbers and/or surfactants, to the foam matrix. Substantially hydrophilic foams that can be utilized in certain embodiments of the invention are available from organizations including the following: Foamex International Inc. (Media, Pa.), Crest Foam Industries, Inc. (Moonachie, N.J.), Rynel, Inc. (Boothbay, Me.), Avitar, Inc. (Canton, Mass., USA), Lendell Manufacturing, Inc. (Charles, Mich., USA), and Copura (Denmark). In addition, certain patents, including U.S. Pat. No. 5,135,472 to Hermann, et al., disclose substantially hydrophilic foams that may be utilized in certain embodiments of the invention. In some embodiments, applicator pad 26 may be formed of a Foamex hydrophobic, reticulated, polyurethane foam.

Applicator pad 26 may include felting or may be non-felted. In addition, applicator pad 26 may include reticulation or may be non-reticulated. In some embodiments, applicator pad 26 may include multiple pad materials. In such embodiments, combinations of any of the above characteristics may be employed. For instance, in one exemplary, multi-material pad, one pad material may be hydrophobic and a second pad material may be hydrophilic.

Figure 12A:
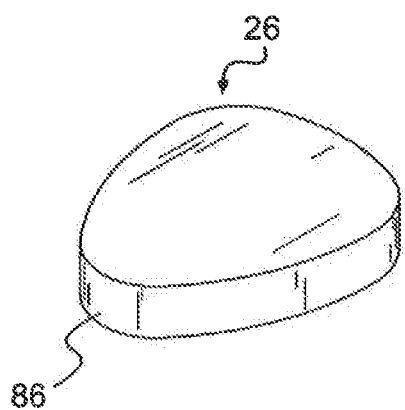
FIGS. 12A-12D illustrate several exemplary disclosed embodiments of applicator pads.
Figure 12B:
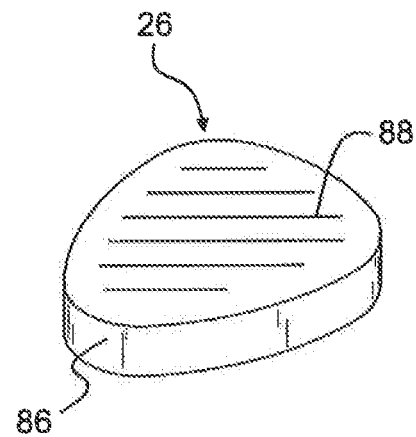

Applicator pad 26 may include a single or multiple layers. In addition, in some embodiments, applicator pad 26 may include slits to facilitate distribution and/or flow of fluid through applicator pad 26. FIGS. 12A-12D illustrate several exemplary embodiments of applicator pad 26 having various combinations of the above-listed features. For example, in some embodiments, applicator pad 26 may comprise a single layer and no slits, as shown in FIG. 12A. In various embodiments, applicator pad 26 may comprise a single layer, which may include slits 88, as shown in FIG. 12B. As illustrated in FIG. 12B, applicator pad 26 may include multiple slits. Further, slits 88 may be provided in a pattern. For example, FIG. 12B shows a pattern of substantially parallel slits 88 oriented at an angle.

Figure 12C:
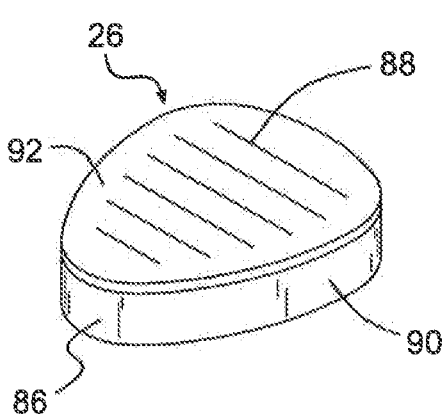
Figure 12D:
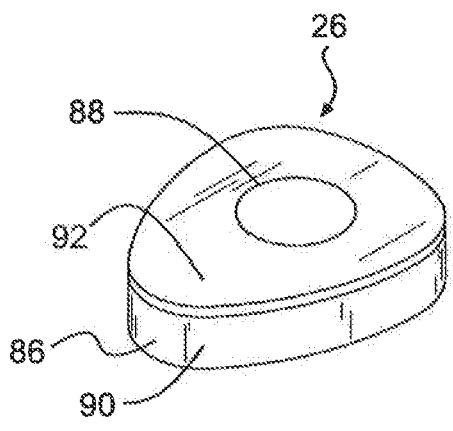

In other embodiments, applicator pad 26 may include multiple layers. As shown in FIGS. 12C and 12D, applicator pad 26 may comprise a base layer 90 and a laminate layer 92. Slits 88 may be provided in base layer 90 and/or in laminate layer 92. FIGS. 12C and 12D illustrate embodiments wherein slits 88 are provided in at least laminate layer 90. FIG. 12C shows a pattern of substantially parallel slits 88 similar to those in FIG. 12B. FIG. 12C illustrates a pattern wherein slits 88 are oriented in a generally lateral direction, as opposed to those in FIG. 12B, which are oriented at an angle. Slits 88 may be disposed at any angle. In addition, slits 88 may be provided in any of a number of shapes, such as slit 88 in FIG. 12D, which is generally circular. Slits 88 may also be formed in other various shapes including, but not limited to, ovals, polygons, etc. Slits 88 may be formed in any suitable fashion, for example, by die/kiss cutting.

In some embodiments, each layer may be formed of a different pad material. In various embodiments, applicator pad 26 may include at least one abrasion layer. In certain applications, an abrasion layer may be used to abrade an area targeted for treatment, for example the epidermis. Abrasion may be performed before, during, and/or after dispensing the fluid. In certain embodiments, abrasion may cause a loosening of certain biological materials, for example body oils, body soils, and/or bacteria, to facilitate treatment of the targeted area. For example, before application of an antiseptic solution, a user may abrade the epidermis of a patient to loosen bacteria in order to improve the efficacy of the antiseptic application process. In certain embodiments, an abrasion layer may comprise more than one layer of material, which may facilitate a greater amount of abrasion and/or abrasion of harder to clean areas.

In certain embodiments, an abrasion layer may comprise various textures and/or weaves, for example, a gauze-like or foam material. In certain embodiments, an exemplary gauze-like material may be made from various materials that facilitate abrasion, including, but not limited to, cotton, rayon, nylon, and/or combinations thereof. Abrasion layer material may be chosen from a number of materials that exhibit varying degrees of abrasiveness. For foam materials, the level of abrasiveness may differ depending on, among other things, the size of the cells/pores. The skin of a premature baby can be thin and fragile, thus an applicator device that comprises an abrasion layer made from nylon or rayon may be preferable to an abrasion layer made from cotton. In certain embodiments, an abrasion layer may comprise a plurality of layers of different materials. In some embodiments, for example foam abrasion layers, the abrasion layer may be flame laminated to base 22 and/or to applicator pad 24.

As illustrated in FIGS. 12C and 12D, laminate layer 92 (which may comprise an abrasion layer) may have a shape that generally corresponds to the shape of base layer 90 of applicator pad 26. However, in certain embodiments, laminate layer 92 may have various other shapes including, but not limited to, circular, oval, rectangular, triangular, polygonal, and the like, or complex shapes including one or more of the same. Layers of applicator pad 26 may be attached to one another by various attachment mechanisms including, but not limited to, adhesive bonding (e.g., using pressure sensitive adhesives), fusion bonding, flame lamination, heat staking, ultrasonic welding, etc. Methods for laminating and/or attaching various materials to applicator pad materials, such as foams, are known in the art. For example, U.S. patent application Ser. No. 10/829,919, U.S. Provisional Application No. 60/464,306, and PCT Serial No, Ser. No. 04/012,474 all disclose methods and apparatuses for attaching materials to polyurethane foam.

Components of applicator system 10, including applicator device 14 and/or packet 12, may be configured to be sterilized in various ways known in the art including, but not limited to, exposure to ethylene oxide ("(Et)$_2$O"), gamma radiation, electron beam, and/or steam. According to various embodiments, the fluid may also be sterilized in various ways known in the art including, but not limited to, filtration, exposure to gamma radiation, electron beam, and/or steam. For example, U.S. Pat. No. 6,682,695 discloses a method for sterilizing a fluid that may be consistent with certain embodiments of the invention.

Various other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A system for applying a fluid, comprising:
a packet containing a fluid, the packet comprising:
first and second opposing packet sides defining therebetween a sealed space containing the fluid;

a frangible area configured to rupture upon compressing the packet to release the fluid from the packet; and a collapsibility feature enabling the first packet side of the packet to invert from a convex position to a concave position upon compressing the packet so that the formerly sealed space is substantially completely collapsed; and an applicator device comprising:

a handle having a proximal end and a distal end, the handle comprising:

a receptacle at the proximal end of the handle, the receptacle configured to receive the packet of the fluid and facilitate expulsion of the fluid from the packet;

a flexible lid configured to sealingly enclose the packet within the receptacle and configured to deflect in response to application of exterior pressure enabling application of the exterior pressure to the packet when disposed within the receptacle to thereby compress the packet to release the fluid from the packet;

a base extending radially outwards at a non-zero angle from the distal end of the handle and configured to direct flow of the released fluid, the base including a distal opening and an outer wall projecting transversely outwards from the base and circumferentially disposed about the distal opening; and an applicator pad configured to be coupled to the base, in fluid communication with an interior portion of the receptacle, wherein a portion of the pad is inserted within the distal opening of the base and a portion of the pad is wrapped around the outer wall to circumscribe the portion of the pad within the distal opening.

2. The system of claim 1, wherein the receptacle has a substantially round shape.

3. The system of claim 2, wherein a central receptacle axis through the substantially round shape of the receptacle is oriented at an angle relative to an axis perpendicular to a plane including the base.

4. The system of claim 3, wherein the angle is approximately 90 degrees.

5. The system of claim 3, wherein the packet has a substantially round shape that is configured to fit concentrically within the substantially round shape of the receptacle.

6. The system of claim 5, wherein the receptacle and the packet have corresponding orienting features that orient the packet with respect to the receptacle.

7. The system of claim 6, wherein the orienting features comprise a structure on the receptacle that deviates from the substantially round shape of the receptacle and a corresponding structure on the packet that deviates from the substantially round shape of the packet.

8. The system of claim 7, wherein the orienting features comprise corresponding protrusions on the receptacle and the packet.

9. The system of claim 8, wherein the protrusion on the receptacle is configured to orient the packet with the protrusion of the packet positioned toward the base.

10. The system of claim 9, wherein the protrusion on the packet comprises the frangible area of the packet.

11. The system of claim 5, wherein the first packet side comprises a first central portion and a first peripheral portion, and the second packet side includes a second central portion and a second peripheral portion;

wherein the first and second packet sides of the packet are sealed to each other at a junction between the first peripheral portion and the second peripheral portion; and wherein the first central portion has a smaller diameter than the second peripheral portion, thereby forming the collapsibility feature.

12. The system of claim 1, wherein the lid is sealingly attached to a rim of the receptacle using an ultrasonic weld.

13. The system of claim 1, wherein the applicator device comprises at least one venting feature configured to allow air flow into or out of the receptacle.

14. The system of claim 13, wherein the venting feature comprises an area at a junction between the flexible lid and the receptacle that is left unsealed.

15. The system of claim 1, wherein the packet contains a fluid comprising a topical antiseptic.

16. The system of claim 15, wherein the topical antiseptic comprises at least one active ingredient chosen from ethanol, isopropyl alcohol, other alcohols, and combinations thereof; benzalkonium chloride; benzethonium chloride; chlorhexidine gluconate; chloroxylenol; cloflucarban; flourosalan; hexachlorophene; hexylresorcinols; iodine containing compounds; biguanide derivatives (or a salt thereof); povidone iodine; povidone iodine with alcohol, ethanol, isopropyl alcohol, other alcohols, and combinations thereof.

17. The system of claim 15, wherein the fluid further comprises a polyoxyethylene (POE)-based nonionic surfactant.

18. The system of claim 17, wherein the nonionic surfactant is at least one surfactant selected from Poloxamer 124, POE (9) lauryl ether, and POE (10) lauryl ether.

19. The system of claim 15, wherein the topical antiseptic comprises a biguanide derivative or a salt thereof.

20. The system of claim 19, wherein the biguanide derivative or salt thereof is olanexidine [1-(3,4-dichlorobenzyl)-5-octylbiguanide] or a salt thereof.

21. The system of claim 20, wherein the topical antiseptic comprises olanexidine gluconate.

22. The system of claim 19, wherein the biguanide derivative or a salt thereof is present at a concentration of about 0.05 to about 5.0% (w/v of biguanide base).

23. The system of claim 15, wherein the fluid further comprises a polyoxyethylene-based nonionic surfactant at a concentration of about 0.05 to about 16% (w/v).

24. The system of claim 1, wherein the applicator device is provided in ready to use form, wherein the packet is sealed within the receptacle and the applicator pad is attached to the base.

* * * * *